United States Patent [19]

Zudkevitch et al.

[11] 4,415,409

[45] Nov. 15, 1983

[54] PROCESS FOR THE SEPARATION OF HIGH BOILING OXYGENATED COMPOUNDS FROM MIXTURES WITH PHENOL AND/OR CRESOL

[75] Inventors: David Zudkevitch, Denville; Stephen E. Belsky, Morris Plains, both of N.J.

[73] Assignee: Allied Corporation, Morris Township, Morris County, N.J.

[21] Appl. No.: 468,242

[22] Filed: Feb. 22, 1983

[51] Int. Cl.$^3$ .......................... B01D 3/40; C07C 37/80
[52] U.S. Cl. ........................................ 203/51; 203/65;
568/366; 568/410; 568/749; 568/835; 568/913
[58] Field of Search ................... 203/65, 51; 568/366, 568/410, 749, 834, 835, 854, 868, 913, 916, 338

[56] References Cited

U.S. PATENT DOCUMENTS

| | | | |
|---|---|---|---|
| 2,583,412 | 1/1952 | Carlson et al. | 203/65 |
| 2,587,753 | 3/1952 | O'Connor et al. | 568/749 |
| 2,824,048 | 2/1958 | Hupe et al. | 568/749 |
| 3,239,434 | 3/1966 | Delaune et al. | 203/65 |
| 4,016,049 | 4/1977 | Fozzard et al. | 568/749 |
| 4,019,965 | 4/1977 | Fozzard | 203/51 |
| 4,115,206 | 9/1978 | Murtha | 568/749 |
| 4,187,152 | 2/1980 | Roth et al. | 568/366 |
| 4,201,632 | 5/1980 | Murtha | 203/51 |

*Primary Examiner*—Wilbur L. Bascomb, Jr.
*Attorney, Agent, or Firm*—Kenneth E. Stroup; Alan M. Doernberg; Gerhard H. Fuchs

[57] ABSTRACT

An extractive distillation process is provided for the separation of phenol and/or cresol from mixtures with high boiling oxygenated compounds such as alkanols, alkanones, cycloalkanones, cycloalkanols, aryl alcohols, aryl ketones or mixtures thereof that have a boiling point of at least about 175° C. The process involves distilling the phenol and/or cresol-high boiling oxygenated compound mixture in the presence of at least one extractive solvent comprising a substituted phenol and/or substituted cresol that has a boiling point between about 195° C. and about 400° C.

11 Claims, No Drawings

PROCESS FOR THE SEPARATION OF HIGH BOILING OXYGENATED COMPOUNDS FROM MIXTURES WITH PHENOL AND/OR CRESOL

BACKGROUND OF THE INVENTION

This invention relates to a novel process for the separation of high boiling oxygenated compounds from mixtures with phenol and/or cresol. The process is especially suitable for separating mixtures of phenol and aryl ketones such as acetophenone. The process is an extractive distillation process that employs substituted phenols and/or substituted cresols as extractive solvents in order to separate phenol and/or cresol from the high boiling oxygenated compounds.

U.S. Pat. No. 4,187,152 discloses a method for separating alkanols, alkanones, cycloalkanols and/or cycloalkanones from mixtures with phenol and/or cresol by distilling said mixtures in the presence of an extractive solvent comprising an alkylated, unmodified cycloalkyl, or aryl derivative of cyclohexanone or cyclohexanol.

U.S. Pat. No. 2,583,412 (Carlson et al.) discloses a method for separating mixtures of close-boiling oxygenated compounds, and particularly low molecular weight close-boiling alcohols, by distilling said mixtures in the present of a large excess of phenol.

Carlson et al. teaches that the volatility of compounds having 1 to 5 carbon atoms in neutral oxygenated mixtures with other oxygenated compounds, all compounds with normal boiling points below 105° C., can be enhanced by the addition of phenol which has a normal boiling point of 180° C. The invention of Carlson et al. discloses the separation of ideal mixtures of oxygenated compounds. For example, mixtures comprising ethanol and isopropanol ae separated by Carlson et al. by enhancing the volatility of ethanol over that of ispropanol. Also, Carlson et al. discloses the separation of mixtures of oxygenated compounds that exhibit positive deviations from ideal mixing such as the separation of ethanol from methyl ethyl ketone. In the first example of Carlson et al., the volatility of ethanol is enhanced only slightly from about 1.16–1.10 to about 1.28–1.38 by subjecting the original mixture to extractive distillation procedures with phenol as the extractive solvent.

The process of the present invention accomplishes separation of acidic phenolic molecules from their mixtures with high molecular weight neutral oxygenated compounds such as alcohols and ketones. The mixtures which may be easily separated by the process of this invention typically exhibit negative deviations from ideal mixtures, and the high molecular weight oxygenated compound of the mixture has at least seven carbon and a boiling point of at least about 175° C.

The process of the present invention is especially suitable for separating mixtures of phenol and aryl ketones such as acetophenone. Mixtures comprising phenol and acetophenone are present in various industrial streams, as for example, in certain streams during the production of phenol by the partial oxidation of cumene. Mixtures of phenol and acetophenone may not be separated by simple distillation procedures due to the formation of a phenol-acetophenone maximum boiling azeotrope. By employing the process of this invention, the volatility of phenol relative to that of acetophenone may be enhanced from a value smaller than unity (i.e., 0.6 or lower) to a value of about 2.3. It is believed that the present invention represents a practical and economical method for obtaining acetophenone-free phenol and phenol-free acetophenone from their mixtures.

BRIEF DESCRIPTION OF THE INVENTION

This invention relates to a process for the separation of a mixture comprised of a first component consisting of at least one member selected from the group consisting of phenol and cresol and a second component having a boiling point of at least about 175° C. consisting of at least one member selected from the group consisting of alkanols, alkanones, cycloalkanones, cycloalkanols, aryl alcohols and aryl ketones wherein said process comprises distilling said mixture in the presence of at least one extractive solvent selected from the group consisting of substituted phenols and cresols having 6 to 25 carbon atoms and a boiling point between about 195° C. and about 400° C. to produce a vapor overhead steam consisting essentially of said first component and a liquid bottoms stream consisting essentially of said second component and said extractive solvent; wherein said mixture may not be separated by simple fractional distillation procedures; wherein said extractive solvent has a boiling point at least about 20° C. above the boiling point of said second component.

DETAILED DESCRIPTION OF THE INVENTION

We have discovered an extractive distillation process for the separation of high boiling oxygenated compounds from their mixtures with phenol and/or cresol. The high boiling compounds which may be separated from their mixtures with phenol and/or cresol have a boiling point of at least about 175° C., and said compounds cannot be separated from mixtures with phenol and/or cresol by general distillation procedures. In many cases, the compounds in the mixture may not be separated by simple distillation procedures because of the formation of a maximum boiling azeotrope. Separation of the high boiling compounds from their mixtures with phenol and/or cresol may be accomplished in accordance with this invention by extractive distillation in the presence of an extractive solvent comprising at least one substituted phenol or cresol having a boiling point between about 195° C. and about 400° C.

Compounds that may be separated from their mixtures with phenol and/or cresol by the process of this invention include substituted or unsubstituted alkanols, alkanones, cycloalkanones, cycloalkanols, aryl alcohols, aryl ketones, or mixtures thereof, which, as stated above, have a boiling point of at least about 175° C. Representative examples of compounds which may be separated from their mixtures with phenol and/or cresol in accordance with this invention include 2-nonanol, 1-ocatanol, 4-decanone, 5-nonanone, 4-ethylcyclohexanone, cyclooctanone, cycloheptanol, acetophenone, o-methylacetophenone, benzyl alcohol, p-methylbenzyl alcohol, etc.

In the preferred embodiments of this invention, the above listed generic classes of compounds are separated from their mixtures with phenol. In many preferred embodiments of this invention, aryl ketones such as substituted or unsubstituted propiophenones, butyrophenones, and acetophenones are separated from mixtures with phenol. An especially preferred embodiment of this invention is the separation of acetophenone from its mixtures with phenol.

Extractive solvents that may be employed for separating the above-described high boiling compounds from mixtures with phenol and/or cresol include at least one substituted phenol or cresol having 6 to 25 carbon atoms and a boiling point between about 195° C. and about 400° C. Representative examples of suitable substituents for the extractive solvents of this invention include linear or branched alkyl groups having 1 to 6 carbon atoms, cycloalkyl groups having 5 to 10 carbon atoms, aryl groups having 6 to 18 carbon atoms, or other similar moieties. It should be appreciated that all said extractive solvents may have one or more hydrogen atoms replaced by a halogen such as chlorine, bromine, fluorine, or iodine. Illustrative examples of extractive solvents that are useful in the process of this invention include 2-t-butylphenol, 2-phenylphenol, 2-cumylphenol, 4-cumylphenol, 2,6-diisopropylphenol, 4-t-butylcatechol, α-phenyl-o-cresol, o-cyclohexylphenol, and other similar solvents.

In selecting an extractive solvent for use in this invention, one should select one or more of the above-described extractive solvents which have a boiling point that is at least about 20° C. above the boiling point of the high boiling oxygenated compound(s). More preferably, the extractive solvent should have a boiling point at least about 50° C. above the boiling point of the high boiling oxygenated compound(s). In many preferred embodiments of this invention, the phenolic or cresolic extractive solvent(s) employed should have a boiling point between about 255° C. and about 350° C., especially for the separation of phenol from mixtures with acetophenone. Illustrative examples of preferred solvents having boiling points in this temperature range include 2-phenylphenol, 4-cumylphenol, 2,6-diisopropylphenol, 4-t-butylphenol and α-phenyl-o-cresol. Especially preferred extractive solvents having a boiling point between about 255° C. and about 350° C. include 2-phenylphenol, 4-cumylphenol or mixtures thereof.

It will be appreciated that if the high boiling oxygenated compound and phenol and/or cresol form an azeotrope, then the extractive solvent need only have a boiling point that is at least about 20° C. above the boiling point of the azeotrope.

Addition of the described extractive solvents to mixtures comprised of phenol and/or cresol and high boiling oxygenated compounds as described above result in binary mixtures between the extractive solvents and high boiling compounds that exhibit negative deviations from ideal mixing. Negative deviations from ideal mixing result from strong attractive forces between the extractive solvent and the particular high boiling compound. Furthermore, the binary mixtures between the same solvents and phenol and/or cresol exhibit ideal mixing behavior with phenol and/or cresol, or preferably exhibit positive deviations from ideal mixing. These positive deviations are manifested by strong repulsive forces between the extractive solvent and phenol and/or cresol. The described combination of mixing phenomena enables one to separate the high boiling oxygenated organic compounds from mixtures with phenol and/or cresol more easily and less expensively than previously thought possible. More particularly, the attractive forces stemming from the negative deviations from ideal mixing of the high boiling oxygenated compound/solvent binaries result in their mixtures having lower vapor pressures than otherwise would result if their mixture exhibited positive deviations from ideal mixing. Thus, the relative volatility between phenol and/or cresol and the high boiling oxygenated compound is enhanced and may also be reversed from being smaller than unity to a value larger than unity with sufficient quantities of the extractive solvent. Therefore, the phenol and/or cresol becomes more volatile due to the negative deviation behavior of the extractive solvent and the high boiling oxygenated compounds.

In practicing this invention, mixtures comprising the high boiling compound(s) and phenol and/or cresol are distilled in a column in the presence of the extractive solvent(s). The amount of extractive solvent that is employed relative to the feed mixture comprising phenol and/or cresol and the high boiling oxygenated compound depends on the pressure, the particular components, the number of trays, reflux ratio and other variables such as economics and efficient energy utilization. In general, however, the molar amount of extractive solvent relative to the feed mixture will range from about 0.5 to about 5.

The process of this invention may be conducted via batch or continuous distillation procedures. If the process is conducted continuously, the extractive solvent may be added to the mixture to be separated prior to introducing said mixture into the column. Alternatively, the extractive solvent may be added separately into the column, or separately in addition to admixture with the mixture to be separated. Typically and preferably, however, the extractive solvent is fed to an intermediate point of the distillation column above the feeding point of the mixture. The mixture to be separated may be added to the column as a vapor or liquid or as a vapor-liquid mixture, with either form being suitable. Processing parameters such as reflux ratio, temperature, pressure, and flow rates of the phenolic and/or cresolic mixture and extractive solvent may easily be determined based upon one's particular needs by those skilled in the art.

The overheads of the extractive distillation will consist essentially of pure phenol or cresol, with very small amounts of the high boiling oxygenated compound and solvent, preferably at least about 99.9 percent phenol or cresol. The bottoms contains extractive solvent and the high boiling oxygenated compound, preferably with minimal amounts or with no phenol or cresol. The bottoms may be, and preferably is, subjected to a subsequent fractional distillation in order to produce an overhead consisting essentially of the high boiling oxygenated compound which was separated from phenol and/or cresol and a bottoms consisting essentially of the extractive solvent. The extractive solvent may then be recycled for use in the continuous process of this invention.

EXAMPLE 1

A liquid mixture containing 30.1 grams phenol and 261.3 grams acetophenone was boiled in a circulating equilibrium still at $6.7 \times 10^3$ Pa absolute pressure and 118.5° C. The equilibrium vapor contained 8.87 mole percent phenol, which commensurates with the relative volatility of 0.657 between phenol and acetophenone. This reversed volatility whereby the phenol with the lower boiling temperature is less volatile than the acetophenone, a compound with a higher boiling point at the same pressure, illustrated that phenol of high purity may not be separated from this mixture by fractional distillation. In a later step 26.3 grams of cumylphenol, mostly 4-cumylphenol were added to 0.8 grams phenol and 8.99 grams acetophenone. The relative volatility between phenol and acetophenone in the resulting ternary mixture at 141° C. and 6.7×10³ Pa absolute pressure was measured to be 2.31. The addition of cumylphenol changed the relative volatility between phenol and acetophenone from being small than one to a value much larger than one. This result demonstrated that phenol can be separated from acetophenone by practicing the extractive distillation process of this invention.

EXAMPLE 2

A liquid mixture that contained 30 mole percent phenol and 70 mole percent acetophenone was continuously fed via Feed 1 onto the 12th tray above the reboiler of a distillation column assembly. Simultaneously, an extractive solvent mixture comprising 95 mole percent 4-cumylphenol and 5 mole percent of other compounds, primarily 2-cumylphenol, was fed via Feed 2 onto the 30th tray above the reboiler of the same column. The distillation column assembly consisted of a reboiler, 52 trays, a condenser and a reflux splitter.

The column was run for several hours at the absolute pressure of 6.7×10³ Pa at the condenser. A reflux ratio of 5:1 was employed. Samples were taken and analyzed. The data, given in Table 1 below, illustrate that phenol of high purity was recovered as the overhead product. The bottoms stream from the distillation consisted essentially of acetophenone and the solvent with less than 1 ppm of phenol, thus providing that complete separation of phenol from its azeotropic mixture with acetophenone can be achieved by practicing the extractive distillation process of this invention.

TABLE 1

| CONCENTRATION (MOLE %) | | | | |
|---|---|---|---|---|
| Compound | Feed 1 | Feed 2 | Overhead | Bottoms |
| Phenol | 30. | — | >99.99 | <1 ppm |
| Acetophenone | 70. | — | <100 ppm | 25.926 |
| Cumyl Phenol | — | 95 | <1 ppm | 70.37 |
| Others | — | 5 | | 3.70 |
| Tray No. from Bottom | 12 | 30 | 52 | 1 |
| Pressure (Pa) | 12.3 × 10³ | 9.5 × 10³ | 6.7 × 10³ | 14.9 × 10³ |
| Flow rate (g/hr.) | 200 | 800 | 60 | 940 |
| Temp. (°C.) | 120 | 100 | 104.3 | 253 |
| Reflux Ratio | | 5:1 | | |

We claim:

1. A process for the separation of a mixture comprised of a first component consisting of at least one member selected from the group consisting of phenol and cresol and a second component having a boiling point of at least about 175° C. consisting of at least one member selected from the group consisting of alkanols, alkanones, cycloalkanones, cycloalkanols, aryl alcohols and aryl ketones; wherein said process comprises distilling said mixture in the presence of at least one extractive solvent selected from the group consisting of substituted phenols and cresols having 6 to 25 carbon atoms and a boiling point between about 195° C. and about 400° C. to produce a vapor overhead stream consisting essentially of said first component and a liquid bottoms stream consisting essentially of said second component and said extractive solvent; wherein said mixture may not be separated by simple fractional distillation procedures; wherein said extractive solvent has a boiling point at least about 20° C. above the boiling point of said second component.

2. A process according to claim 1 wherein said first component is phenol.

3. A process according to claim 2 wherein said second component is an aryl ketone.

4. A process according to claim 3 wherein said aryl ketone is acetophenone.

5. A process according to claim 4 wherein said extractive solvent comprises at least one substituted phenol having a boiling point between about 255° C. and about 350° C.

6. A process according to claim 5 wherein said extractive solvent comprises a mixture of 2-cumylphenol and 4-cumylphenol.

7. A process according to claim 5 wherein said extractive solvent is 4-cumylphenol.

8. A process according to claim 1 wherein said second component is an aryl ketone.

9. A process according to claim 1 wherein said extractive solvent comprises at least one substituted phenol having a boiling point between about 255° C. and about 350° C.

10. A process according to claim 9 wherein said extractive solvent comprises a mixture of 2-cumylphenol and 4-cumylphenol.

11. A process according to claim 9 wherein said extractive solvent is 4-cumylphenol.

* * * * *